(12) United States Patent
Golanov et al.

(10) Patent No.: US 11,376,421 B2
(45) Date of Patent: Jul. 5, 2022

(54) NEUROSTIMULATION INDUCED MEDICINE DEVICES AND RELATED METHODS OF USE

(71) Applicant: THE METHODIST HOSPITAL SYSTEM, Houston, TX (US)

(72) Inventors: Eugene V. Golanov, Houston, TX (US); Gavin W. Britz, Houston, TX (US); Philip John Horner, Houston, TX (US); Tatiana Wolfe, Hilliard, OH (US)

(73) Assignee: The Methodist Hospital System, Houston, TX (US)

( * ) Notice: Subject to any disclaimer, the term of this patent is extended or adjusted under 35 U.S.C. 154(b) by 0 days.

(21) Appl. No.: 16/762,542

(22) PCT Filed: Nov. 9, 2018

(86) PCT No.: PCT/US2018/059993
§ 371 (c)(1),
(2) Date: May 8, 2020

(87) PCT Pub. No.: WO2019/094698
PCT Pub. Date: May 16, 2019

(65) Prior Publication Data
US 2020/0360683 A1  Nov. 19, 2020

Related U.S. Application Data

(60) Provisional application No. 62/583,778, filed on Nov. 9, 2017.

(51) Int. Cl.
*A61N 1/05* (2006.01)
*A61N 1/36* (2006.01)
(Continued)

(52) U.S. Cl.
CPC ......... *A61N 1/0519* (2013.01); *A61M 16/045* (2014.02); *A61M 16/0488* (2013.01);
(Continued)

(58) Field of Classification Search
CPC .... A61N 1/0517; A61N 1/0519; A61N 1/086; A61N 1/36053; A61N 1/3614; A61M 16/045; A61M 16/0488
See application file for complete search history.

(56) References Cited

U.S. PATENT DOCUMENTS

| 4,351,330 A | * | 9/1982 | Scarberry | G02B 27/01 128/207.15 |
| 5,651,378 A | * | 7/1997 | Matheny | A61N 1/36014 128/898 |

(Continued)

OTHER PUBLICATIONS

International Search Report and Written Opinion in PCT/US2018/059993, dated Jan. 22, 2019. 8 pages.
(Continued)

*Primary Examiner* — Carl H Layno
*Assistant Examiner* — Anh-Khoa N Dinh
(74) *Attorney, Agent, or Firm* — Meunier Carlin & Curfman LLC

(57) ABSTRACT

Example neurostimulation induced medicine devices and methods of use are described herein. An example endotracheal device can include an elongate tubular member having a proximal end and a distal end, an inflatable cuff arranged between the proximal and distal ends of the elongate tubular member, and an electrode array disposed in proximity to an exterior surface of the inflatable cuff. The inflatable cuff can be configured to expand to contact a subject's tracheal wall. Additionally, the electrode array can include a plurality of flexible electrodes, where a set of the flexible electrodes anatomically align with a region of the subject's tracheal wall for selectively targeting vagus nerve activity.

25 Claims, 10 Drawing Sheets

(51) Int. Cl.
*A61N 1/04* (2006.01)
*A61N 1/08* (2006.01)
*A61M 16/04* (2006.01)

(52) U.S. Cl.
CPC ........... *A61N 1/086* (2017.08); *A61N 1/3614* (2017.08); *A61N 1/36053* (2013.01)

(56) References Cited

U.S. PATENT DOCUMENTS

| | | | | |
|---|---|---|---|---|
| 6,292,689 | B1* | 9/2001 | Wallace | A61B 5/029 600/547 |
| 6,381,499 | B1 | 4/2002 | Taylor et al. | |
| 6,532,388 | B1* | 3/2003 | Hill | A61N 1/0517 607/2 |
| 7,840,278 | B1 | 11/2010 | Puskas | |
| 2002/0032468 | A1* | 3/2002 | Hill | A61N 1/362 607/2 |
| 2002/0188332 | A1* | 12/2002 | Lurie | A61M 16/04 607/48 |
| 2003/0074039 | A1* | 4/2003 | Puskas | A61N 1/056 607/118 |
| 2010/0094376 | A1* | 4/2010 | Penner | A61N 1/0517 607/42 |
| 2010/0113939 | A1* | 5/2010 | Mashimo | A61B 5/1076 600/470 |
| 2013/0245486 | A1 | 9/2013 | Simon et al. | |

OTHER PUBLICATIONS

Abulaiti, Alimujiang, et al. "Influence of fastigial nucleus stimulation on heart rate variability of surgically induced myocardial infarction rats: fastigial nucleus stimulation and autonomous nerve activity." Heart and vessels 26.6 (2011): 654-662.
Ay, Ilknur, et al. "Transcutaneous cervical vagus nerve stimulation ameliorates acute ischemic injury in rats." Brain stimulation 9.2 (2016): 166-173.
Ay, Ilknur, Vitaly Napadow, and Hakan Ay. "Electrical stimulation of the vagus nerve dermatome in the external ear is protective in rat cerebral ischemia." Brain stimulation 8.1 (2015): 7-12.
Cai, Peter Y., et al. "Vagus nerve stimulation in ischemic stroke: old wine in a new bottle." Frontiers in neurology 5 (2014): 107.
Chen, Ning, et al. "Neuroprotective effects of vagus nerve stimulation on hippocampal neurons in intractable epilepsy." Medical hypotheses 81.6 (2013): 1066-1068.
Chowdhury T, Mendelowith D, Golanov E, Spiriev T, Arasho B, Sandu N, Sadr-Eshkevari P, Meuwly C, Schaller B. Trigeminocardiac reflex: the current clinical and physiological knowledge. J Neurosurg Anesthesiol. 2015;27(2):136-47. Epub Jan. 21, 2015. doi:10.1097/ana.0000000000000065. PubMed PMID: 25602626.
Ekici, Fatih, et al. "The effects of vagal nerve stimulation in focal cerebral ischemia and reperfusion model." Turkish neurosurgery 23.4 (2013): 451-457.
Feng, Ling-Bo, et al. "MicroRNA involvement in mechanism of endogenous protection induced by fastigial nucleus stimulation based on deep sequencing and bioinformatics." BMC medical genomics 8.1 (2015): 79, 1-9.
Galea, Elena, et al. "Cerebellar stimulation reduces inducible nitric oxide synthase expression and protects brain from ischemia." American Journal of Physiology-Heart and Circulatory Physiology 274.6 (1998): H2035-H2045.
Galea, Elena, et al. "Stimulation of cerebellar fastigial nucleus inhibits interleukin-1β-induced cerebrovascular inflammation." American Journal of Physiology-Heart and Circulatory Physiology 275.6 (1998): H2053-H2063.
Glickstein, Sara B., Christopher P. Ilch, and Eugene V. Golanov. "Electrical stimulation of the dorsal periaqueductal gray decreases volume of the brain infarction independently of accompanying hypertension and cerebrovasodilation." Brain research 994.2 (2003): 135-145.

Glickstein, Sara B., et al. "Stimulation of the subthalamic vasodilator area and fastigial nucleus independently protects the brain against focal ischemia." Brain research 912.1 (2001): 47-59.
Glickstein, Sara B., Eugene V. Golanov, and Donald J. Reis. "Intrinsic neurons of fastigial nucleus mediate neurogenic neuroprotection against excitotoxic and ischemic neuronal injury in rat." Journal of Neuroscience 19.10 (1999): 4142-4154.
Golanov E, Chen B, Shiflett JM, Esposito E, Parent A. Uncoupling protein 4: possible involvement in neurogenic neuroprotection. FASEB. 2003, A1069.
Golanov E, Li C, Britz GW, Narayan RK. Early Trigeminal Nerve Stimulation Reduces Brain Edema and Lesion Volumes Following Traumatic Brain Injury. AANS. 2016, 23544.
Golanov EV, Sitton M, Shiflett MJ, Parent AD. Diving response is neuroprotective. Society for Neuroscience. 2004;821.7.
Golanov, Eugene V., and Donald J. Reis. "A role for KATP+-channels in mediating the elevations of cerebral blood flow and arterial pressure by hypoxic stimulation of oxygen-sensitive neurons of rostral ventrolateral medulla." Brain research 827.1-2 (1999): 210-214.
Golanov, Eugene V., and Donald J. Reis. "Neuroprotective electrical stimulation of cerebellar fastigial nucleus attenuates expression of periinfarction depolarizing waves (PIDs) and inhibits cortical spreading depression." Brain research 818.2 (1999): 304-315.
Golanov, Eugene V., and Ping Zhou. "Neurogenic neuroprotection." Cellular and molecular neurobiology 23.4 (2003): 651-663.
Golanov, Eugene V., Fang Liu, and Donald J. Reis. "Stimulation of cerebellum protects hippocampal neurons from global ischemia." Neuroreport 9.5 (1998): 819-824.
Golanov, Eugene V., James M. Shiflett, and Gavin W. Britz. "Diving response in rats: role of the subthalamic vasodilator area." Frontiers in neurology 7 (2016): 157.
Golanov, Eugene V., John D. Christensen, and Donald J. Reis. "Role of potassium channels in the central neurogenic neuroprotection elicited by cerebellar stimulation in rat." Brain research 842.2 (1999): 496-500.
Goldstein KR, Golanov EV, Iadecola C, Anrather J. Fastigial Nucleus Stimulation increases BrdU Immunoreactivity in the Paraventricular Nucleus of the Rat. Society for Neuroscience. 2002;230.11.
Hennerici, Michael G., Rolf Kern, and Kristina Szabo. "Non-pharmacological strategies for the treatment of acute ischaemic stroke." The Lancet Neurology 12.6 (2013): 572-584.
Henninger, Nils, and Marc Fisher. "Stimulating circle of Willis nerve fibers preserves the diffusion-perfusion mismatch in experimental stroke." Stroke 38.10 (2007): 2779-2786.
Hiraki, Teruyuki, Wesley Baker, and Joel H. Greenberg. "Effect of vagus nerve stimulation during transient focal cerebral ischemia on chronic outcome in rats." Journal of neuroscience research 90.4 (2012): 887-894.
Huang, Li-Gang, et al. "Micro RNA-29c Correlates with Neuroprotection Induced by FNS by Targeting Both Birc2 and Bak 1 in Rat Brain after Stroke." CNS neuroscience & therapeutics 21.6 (2015): 496-503.
Jiang, Ying, et al. "Auricular vagus nerve stimulation promotes functional recovery and enhances the post-ischemic angiogenic response in an ischemia/reperfusion rat model." Neurochem Int. 2016;97:73-82. Epub Mar. 12, 2016. doi:10.1016/j.neuint.2016.02.009. PubMed PMID: 26964767.
Jiang, Ying, et al. "PPARγ upregulation induced by vagus nerve stimulation exerts anti-inflammatory effect in cerebral ischemia/reperfusion rats." Medical science monitor: international medical journal of experimental and clinical research 21 (2015): 268.
Jiang, Ying, et al. "Vagus nerve stimulation attenuates cerebral ischemia and reperfusion injury via endogenous cholinergic pathway in rat." PloS one 9.7 (2014) e102342.
Kumaria, Ashwin, and Christos M. Tolias. "Is there a role for vagus nerve stimulation therapy as a treatment of traumatic brain injury?." British journal of neurosurgery 26.3 (2012): 316-320.
Li C, Golanov E, Mehan N, Narayan RK. Neuroprotective effects of trigeminal nerve stimulation in traumatic brain injury. MHSRS. 2015. 7:6792.

(56) References Cited

OTHER PUBLICATIONS

Liu, Bin, et al. "Electrical stimulation of cerebellar fastigial nucleus protects against cerebral ischemic injury by PPARγ upregulation." Neurological research 39.1 (2017): 23-29.
Mandel, Mauricio, et al. "Neurogenic neuroprotection: clinical perspectives." Functional neurology 27.4 (2012): 207.
Matheny, Robert G., and Carl J. Shaar. "Vagus nerve stimulation as a method to temporarily slow or arrest the heart." The Annals of thoracic surgery 63.6 (1997): S28-S29. Abstract.
Meuwly, C., et al. "Trigeminal cardiac reflex: new thinking model about the definition based on a literature review." Medicine 94.5 (2015), e484.
Miyamoto, Osamu, et al. "Mechanisms of the anti-ischemic effect of vagus nerve stimulation in the gerbil hippocampus." Neuroreport 14.15 (2003): 1971-1974.
Nalls T, Garabedian R, Wallace M, Golanov E. Stimulation of sphenopalatine ganglion (SPG) decreases volume of the infarction triggered by permanent middle cerebral artery occlusion (MCAO). Society for Neuroscience. 2005:702.10.
Neren, Daniel, et al. "Vagus nerve stimulation and other neuromodulation methods for treatment of traumatic brain injury." Neurocritical care 24.2 (2016): 308-319.
Pang, Xiao-Min, et al. "Fastigial nucleus stimulation regulates neuroprotection via induction of a novel micro RNA, rno-miR-676-1, in middle cerebral artery occlusion rats." Journal of neurochemistry 133.6 (2015): 926-934.
Qi, Lei, et al. "Ghrelin protects rats against traumatic brain injury and hemorrhagic shock through upregulation of UCP2." Annals of Surgery 260.1 (2014): 169-178.
Reis, Donald J., et al. "Brief electrical stimulation of cerebellar fastigial nucleus conditions long-lasting salvage from focal cerebral ischemia: conditioned central neurogenic neuroprotection." Brain research 780.1 (1998): 161-165.
Reis, Donald J., et al. "Central neurogenic neuroprotection: central neural systems that protect the brain from hypoxia and ischemia." Annals of the New York Academy of Sciences 835.1 (1997): 168-186.
Rollins, Shadon, Betty Chen, and Eugene Golanov. "Possible role of cerebellar fastigial nucleus in preconditioned neuroprotection." Journal of Cerebral Blood Flow & Metabolism (2005):334.
Schellinger, Peter D., and Martin Köhrmann. "Current acute stroke trials and their potential impact on the therapeutic time window." Expert review of neuro therapeutics 12.2 (2012): 169-177.
Shiflett, J. M., A. D. Parent, and E. V. Golanov. "Forehead stimulation decreases volume of the infarction triggered by permanent occlusion of middle cerebral artery in rats." J Neurol Stroke 2.00067 (2015): 10-15406.
Silverman, Harold A., et al. "Brain region-specific alterations in the gene expression of cytokines, immune cell markers and cholinergic system components during peripheral endotoxin-induced inflammation." Molecular medicine 20.1 (2014): 601-611.
Sun, Zhenghui, et al. "The effect of right vagus nerve stimulation on focal cerebral ischemia: an experimental study in the rat." Brain stimulation 5.1 (2012): 1-10.
Tang, Weiju, et al. "The effect of pre-condition cerebella fastigial nucleus electrical stimulation within and beyond the time window of thrombolytic on ischemic stroke in the rats." PloS one 10.5 (2015): e0128447.
Wang, Jian, et al. "Electrical stimulation of cerebellar fastigial nucleus: mechanism of neuroprotection and prospects for clinical application against cerebral ischemia." CNS neuroscience & therapeutics 20.8 (2014): 710-716.
Winship, Ian R. "Cerebral collaterals and collateral therapeutics for acute ischemic stroke." Microcirculation 22.3 (2015): 228-236.
Xiang, Yao-xian, et al. "Electrical stimulation of the vagus nerve protects against cerebral ischemic injury through an anti-infammatory mechanism." Neural regeneration research 10.4 (2015): 576.
Zhang, Lei, Mingkui Zhao, and Ru-Bo Sui. "Cerebellar fastigial nucleus electrical stimulation alleviates depressive-like behaviors in post-stroke depression rat model and potential mechanisms." Cellular Physiology and Biochemistry 41.4 (2017): 1403-1412.
Zhou, Long, et al. "Neuroprotective effects of vagus nerve stimulation on traumatic brain injury." Neural regeneration research 9.17 (2014): 1585.
Zhou, Ping, et al. "Electrical stimulation of cerebellar fastigial nucleus protects rat brain, in vitro, from staurosporine-induced apoptosis." Journal of neurochemistry 79.2 (2001): 328-338.
Zhou, Ping, et al. "Mitochondria are involved in the neurogenic neuroprotection conferred by stimulation of cerebellar fastigial nucleus." Journal of neurochemistry 95.1 (2005): 221-229.

\* cited by examiner

NEUROSTIMULATION INDUCED MEDICINE DEVICES AND RELATED METHODS OF USE

CROSS-REFERENCE TO RELATED APPLICATIONS

This application is a national stage application filed under 35 U.S.C 0 371 of PCT/US2018/059993 filed Nov. 9, 2018, which claims the benefit of U.S. provisional patent application No. 62/583,778, filed on Nov. 9, 2017, and entitled "NEUROSTIMULATION INDUCED MEDICINE DEVICES AND RELATED METHODS OF USE," the disclosures of which are expressly incorporated herein by reference in their entireties.

BACKGROUND

Published data indicates that direct manipulation of vagal electrical activity has remarkable therapeutic potential for the modulation of inflammation, control of brain perfusion, reduction of edema, and facilitation of endogenous repair in the setting of brain injury, stroke, general surgery and emergency care. Conventional technologies for stimulating vagal nerve activity, however, are not useable and/or practical in many surgical settings and/or to provide acute treatment. For example, conventional, non-invasive stimulation technologies use magnetic or similar approaches but lack specificity and are bulky, variable and difficult or impossible to manage or introduce in the acute post-trauma, stroke, or surgical setting. Additionally, invasive stimulation technologies are common and numerous but require an open-neck surgical procedure that is precluded in the acute management stream in patient care for acute trauma and stroke and would also not be an option for neither pre-surgical management or post stroke acute care.

SUMMARY

An example endotracheal device is described herein. The endotracheal device can include an elongate tubular member having a proximal end and a distal end, an inflatable cuff arranged between the proximal and distal ends of the elongate tubular member, and an electrode array disposed in proximity to an exterior surface of the inflatable cuff. The inflatable cuff can be configured to expand to contact a subject's tracheal wall. Additionally, the electrode array can include a plurality of flexible electrodes, where a set of the flexible electrodes anatomically align with a region of the subject's tracheal wall for selectively targeting vagus nerve activity.

In some implementations, each of the flexible electrodes can be configured to stretch as the inflatable cuff expands to contact the subject's tracheal wall.

Alternatively or additionally, the flexible electrodes can form an annular, spiral, concentric, or curved pattern on the exterior surface of the inflatable cuff.

Alternatively or additionally, each of the flexible electrodes can have a shape that allows contact with the subject's tracheal wall. Optionally, in some implementations, a diameter or side length of each of the flexible electrodes is between about 0.1 mm and about 1.0 mm.

Alternatively or additionally, the endotracheal device can further include a plurality of inflatable cuffs arranged between the proximal and distal ends of the elongate tubular member. Additionally, the electrode array can optionally be arranged across respective exterior surfaces of the plurality of inflatable cuffs.

Alternatively or additionally, the inflatable cuff can include a first inflatable portion and a second inflatable portion. The first inflatable portion can include the electrode array, and the second inflatable portion can include a plurality of openings corresponding to the flexible electrodes. For example, the second inflatable portion can be configured to contact the subject's tracheal wall, and the flexible electrodes can be configured to extend through the corresponding openings of the second inflatable portion to contact the subject's tracheal wall.

Alternatively or additionally, the first inflatable portion can include a plurality of protrusions, and the flexible electrodes can be patterned on a surface of the protrusions.

Alternatively or additionally, each of the first and second inflatable portions can be configured for independent pressure regulation.

Alternatively or additionally, the endotracheal device can further include a stimulus generator operably coupled with the electrode array, and a controller operably coupled with the stimulus generator. The controller can include a processor and memory. The controller can be configured to control the stimulus generator to deliver a stimulus signal to at least one of the flexible electrodes. Optionally, each of the flexible electrodes can be individually addressable by the controller.

Alternatively or additionally, the stimulus generator and the electrode array can be operably coupled by a plurality of flexible conductors, each respective flexible conductor extending between one or more of the flexible electrodes and the stimulus generator. Optionally, each of the flexible conductors can be configured to stretch as the inflatable cuff expands to contact the subject's tracheal wall.

Alternatively or additionally, the controller can be further configured to monitor impedance detected at one or more of the flexible electrodes. In some implementations, the controller can be further configured to control pressure of the inflatable cuff based on the detected impedance.

Alternatively or additionally, the controller can be further configured to identify the set of the flexible electrodes by sequentially delivering test stimulus signals to one or more of the flexible electrodes and monitoring the subject's physiological feedback signal detected in response to the test stimulus signals. For example, the subject's physiological feedback signal can be an electrocardiogram, encephalogram, arterial pressure, or galvanic skin response.

Alternatively or additionally, the controller can be further configured to control the stimulus generator to deliver the stimulus signal to the set of the flexible electrodes, where the stimulus signal is configured to stimulate the vagus nerve or surrounding tissue structures. Optionally, the controller can be further configured to optimize at least one parameter of the stimulus signal by monitoring the subject's physiological feedback signal. For example, the controller can optimize a frequency or current intensity of the stimulus signal. Alternatively or additionally, the controller can optimize a number of electrodes in the set of the flexible electrodes that are used to deliver the stimulus signal.

Alternatively or additionally, the endotracheal device can further include a holding inflatable cuff arranged distally with respect to the inflatable cuff. The holding inflatable cuff can be configured to secure the elongate tubular member within the subject's trachea.

Alternatively or additionally, the flexible electrodes can be formed of an electromagnetically compatible (EMC)

material compatible with magnetic resonance imaging (MRI), i.e., MRI conditional flexible electrodes.

An example method for modulating vagus nerve activity is described herein. The method can include inserting an endotracheal device into the subject's trachea, delivering electrical stimulation to the subject's tracheal wall through an electrode array of the endotracheal device, and modulating the subject's vagus nerve activity using the electrical stimulation.

In some implementations, the method can further include treating a medical condition by modulating the subject's vagus nerve activity. For example, the medical condition can be stroke, traumatic brain injury, shock, hemorrhage, general surgery, brain and spinal surgery, a general anesthesia procedure, cardiac surgery, cardiac surgery under cardiopulmonary bypass, extracorporeal bypass surgery, or comatose state. In some implementations, the medical condition is a transient condition and presents during a post surgical recovery period. In other implementations, the medical condition is a long term condition such as a comatose or vegetative state, for example. Electrical stimulation can be delivered one time or repeatedly (e.g., recurrent stimulation) to treat the medical condition.

Alternatively or additionally, the method can further include tailoring at least one parameter of the electrical stimulation based on the medical condition.

Alternatively or additionally, the method can further include monitoring a physiological feedback signal of the subject. For example, the physiological feedback signal can be an electrocardiogram, encephalogram, arterial pressure, or galvanic skin response. Alternatively or additionally, the method can further include tailoring at least one parameter of the electrical stimulation based on the physiological feedback signal.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

In FIG. 5, the heart rate is labeled 502, and the stimulation current is labeled 504. The stimulation current was 60 mA (cathodic), pulse-width=100 µs, and frequency=0.5 Hz.

In FIG. 6, the heart rate is labeled 602, and the stimulation current is labeled 604. The stimulation pulses were cathodic currents=30 mA, 15 mA, 5 mA, and 75 mA, pulse-width=100 µs, and frequency=0.5 Hz.

In FIG. 7, the heart rate is labeled 702, and the stimulation current is labeled 704. The stimulation train was intermittently active with current=30 mA (cathodic), pulse-width=100 µs, and frequency=1 Hz.

As shown in FIG. 8, with increasing current intensity, the drop in heart rate is larger for both direct and trans-tracheal vagus nerve stimulation. For the measurements shown in FIG. 8, pulse-width was 100 µs, tracheal stimulation frequency was 0.5 Hz, and cuff stimulation frequency was 1 Hz.

DETAILED DESCRIPTION

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. Ranges may be expressed herein as from "about" one particular value, and/or to "about" another particular value. When such a range is expressed, an aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. While implementations will be described for alleviating brain damage due to injury, stroke, or surgical complication using neurostimulation induced medicine (nSIM) devices, it will become evident to those skilled in the art that the implementations are not limited thereto, but are applicable for treating other medical conditions by direct electrical stimulation of the vagus nerve and/or surrounding tissue structures.

Described herein are neurostimulation induced medicine (nSIM) devices and related methods of use. The nSIM devices described herein are minimally invasive and used for direct electrical stimulation of a subject's (e.g., patient's)

vagus nerve or surrounding tissue structures to modulate brain and immune function. It is possible to treat a medical condition by modulating brain and immune function. For example, brain damage due to injury, stroke, or surgical complication can be alleviated through such modulation.

Example Neurostimulation Induced Medicine Devices

Figure 1A:
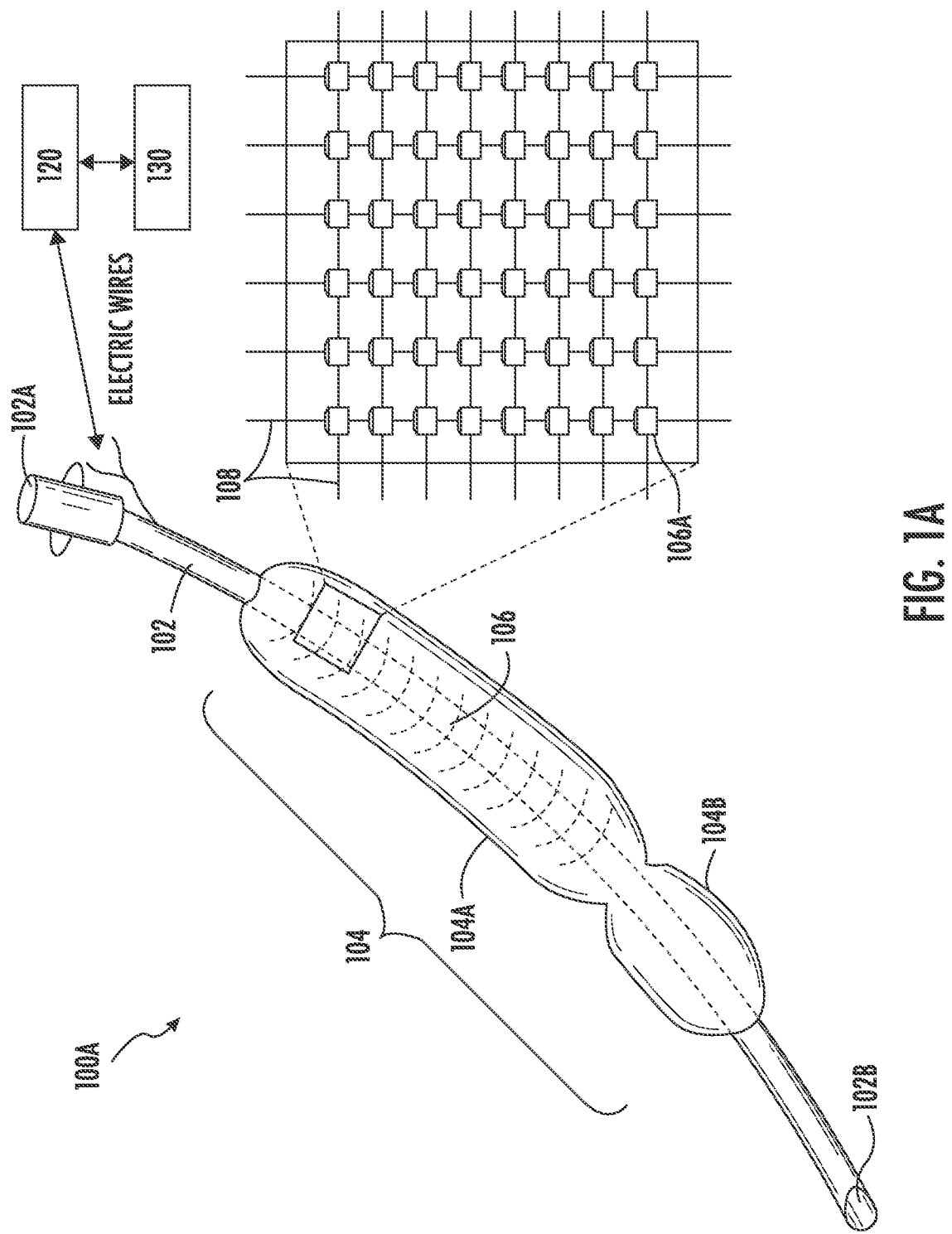
FIG. 1A is a diagram of an example endotracheal device according to an implementation described herein.

Referring now to FIG. 1A, an example endotracheal device 100A (e.g., an nSIM device) is shown. The endotracheal device 100A can include an elongate tubular member 102 having a proximal end 102A and a distal end 102B. The elongate tubular member 102 can have a diameter and length appropriate for newborn to adults (e.g., from 5.5 cm to 21 cm from lip). The endotracheal device 100A can also include an inflatable cuff 104 arranged between the proximal and distal ends of the elongate tubular member 102, and an electrode array 106 disposed in proximity to an exterior surface of the inflatable cuff 104. For example, in FIG. 1A, the electrode array 106 is arranged on the exterior surface of the inflatable cuff 104. The inflatable cuff 104 can be configured to expand to contact a subject's tracheal wall.

Additionally, the electrode array 106 can include a plurality of flexible electrodes 106A, where a set of the flexible electrodes anatomically align with a region of the subject's tracheal wall for selectively targeting vagus nerve activity. As described herein, a stimulus signal can be applied to one or more of the flexible electrodes 106A in order to electrically stimulate the subject's vagus nerve and/or surrounding tissue structures. As used herein, a "set of the flexible electrodes" can include one or more of the flexible electrodes 106A of the electrode array 106. The set of the flexible electrodes can optionally be a subset (e.g., less than all) of the flexible electrodes 106A. In other words, the flexible electrodes 106A are arranged on the exterior surface of the inflatable cuff 104, which is designed to fit patients of various sizes, such that the flexible electrodes provide coverage of the area of the trachea in patients of different size. At least some of the flexible electrodes 106A (i.e., the set of flexible electrodes) in the electrode array 106 anatomically align with a region of the tracheal wall for selectively targeting vagus nerve activity (i.e., region of interest) in any given subject. The vagus nerve and/or surrounding tissue structures can be directly electrically stimulated by applying the stimulus signal in the region of interest. It should be understood that the region of interest is a relatively small but intimate target, and the location and/or size of the region of interest may vary from patient-to-patient. By providing an array of addressable flexible electrodes, the region of interest can be targeted in each particular patient.

In some implementations, the endotracheal device 100A includes a single inflatable cuff arranged between the proximal and distal ends of the elongate tubular member 102. In other implementations, the endotracheal device 100A includes a plurality of inflatable cuffs arranged between the proximal and distal ends of the elongate tubular member 102. For example, as shown in FIG. 1A, the endotracheal device 100A includes inflatable cuff 104A, which has the electrode array 106 arranged on an exterior surface of thereof, and a holding inflatable cuff 104B arranged distally with respect to the inflatable cuff 104A. The holding inflatable cuff 104B can be configured to secure the elongate tubular member 102 within the subject's trachea. The holding cuff 104B (i.e., cuff at the lower or distal end 102B of the elongate tubular member 102) can be a "high" or "low" pressure type. The inflatable cuff 104A (i.e., cuff at the upper or proximal end 102A of the elongate tubular member 102) can cover the portion of the elongate tubular member 102 just below the subject's larynx. Each cuff 104A, 104B can have separate tubing and/or pressure regulators for inflation. Alternatively or additionally, in some implementations, the electrode array 106 can optionally be arranged across respective exterior surfaces of a plurality of inflatable cuffs (e.g., the inflatable cuff 104A of FIG. 1A can include a plurality of inflatable cuffs similar to endotracheal devices 200D or 200E of FIG. 2).

The exterior surface of the inflatable cuff 104A and/or the holding cuff 104B can be covered with a matrix of elastic or flexible electrodes. This disclosure contemplates that the electrodes can be thin, flat, and/or elastic. In some implementations, the matrix can include round, square, or annular electrodes with the fixed diameter (or side length) of about 0.1 millimeter (mm) to about 1 mm positioned at the nodes of the matrix. The matrix can optionally be made of thin film transistors (TFT), which can be controlled with a controller (e.g., controller 130 of FIG. 1A) capable of regulating voltage in each electrode. The connections between matrix nodes (i.e., electrodes) can be made with elastic (expandable) conductors, which can stretch with the expanding cuff without affecting the resistance of the conductors. For example, each of the flexible electrodes 106A can be configured to stretch as the inflatable cuff 104A expands to contact the subject's tracheal wall. In some implementations, the flexible electrodes 106A can form a spiral, concentric, annular, or curved pattern on the exterior surface of the inflatable cuff 104A. Optionally, one or more of the flexible electrodes 106A can have a shape that allows contact with the subject's tracheal wall. For example, a flexible electrode can be round, annular, or square-shaped. It should be understood that round, annular, and square-shaped electrodes are provided only as examples. This disclosure contemplates that the flexible electrodes 106A described herein can have any shape that allows contact with the subject's tracheal wall. Optionally, in some implementations, a diameter or side length of each of the flexible electrodes 106A is between about 0.1 mm and about 1.0 mm. This disclosure contemplates that the diameter or side length of the flexible electrodes 106A can have sizes other than those provided as examples. Additionally, this disclosure contemplates that the flexible electrodes 106A in the electrode array 106 can have the same or different shapes and/or sizes.

The flexible electrodes 106A can optionally be formed of an electromagnetically compatible (EMC) material compatible with magnetic resonance imaging (MRI), i.e., MRI conditional flexible electrodes. Example EMC materials include, but are not limited to, titanium, cobalt-chromium, gold, platinum, stainless steel, or copper. It should be understood that titanium, cobalt-chromium, gold, platinum, stainless steel, and copper are only provided as example EMC materials and that this disclosure contemplates using other EMC materials.

Alternatively or additionally, the flexible electrodes 106A can optionally be formed of a radio translucent material. Example radio translucent materials include, but are not limited to, intrinsically conductive polymers (ICPs) or conductive medical grade plastics, conductive carbon fibers, molecular crystals, molecularly doped crystals, or porcelain. It should be understood that intrinsically conductive polymers (ICPs) or conductive medical grade plastics, conductive carbon fibers, molecular crystals, molecularly doped crystals, and porcelain are only provided as example radio translucent materials and that this disclosure contemplates using other radio translucent materials.

In some implementations, the endotracheal device 100A can further include a stimulus generator 120 operably coupled with the electrode array 106. For example, the stimulus generator 120 and the electrode array 106 can be operably coupled by a plurality of flexible conductors 108, each respective flexible conductor 108 extending between one or more of the flexible electrodes 106A and the stimulus generator 120. Optionally, each of the flexible conductors 108 can be configured to stretch as the inflatable cuff 104 expands to contact the subject's tracheal wall.

Stimulus generators are well-known in the art and are not described in detail herein. The stimulus generator 120 can be configured to deliver stimulus signals (e.g., electrical stimulation) to the flexible electrodes 106A. Optionally, the stimulus generator 120 can be a voltage source or current source. The stimulus generator 120 can be configured to supply a voltage to the flexible electrodes 106A. In some implementations, the stimulus generator 120 can include programmable logic (e.g., processor and memory such as basic configuration of computing device 300 of FIG. 3) for controlling the stimulus generator 120. For example, the stimulus generator 120 can be configured to select the parameters of the electrical stimulation (e.g., frequency, current intensity, waveform shape, etc.). As described herein, various frequencies, current intensities, waveform shapes, and/or number of electrodes can be used to provide stimulation. Optionally, these characteristics or parameters can be tailored to the medical condition being treated (e.g., stroke versus traumatic brain injury) and/or to the individual patient.

In some implementations, the endotracheal device 100A can further include a controller 130 operably coupled with the stimulus generator 120. The stimulus generator 120 can be operably coupled to a controller 130 using a communication link. This disclosure contemplates the communication link is any suitable communication link. For example, a communication link can be implemented by any medium that facilitates data exchange between the stimulus generator 120 and the controller 130 including, but not limited to, wired, wireless and optical links. Example communication links include, but are not limited to, a LAN, a WAN, a MAN, Ethernet, the Internet, or any other wired or wireless link such as Bluetooth, Wi-Fi, ZigBee, Wi-Max, 3G or 4G. The controller 130 can include a processor and memory (e.g., computing device 300 of FIG. 3). The controller 130 can be configured to control the stimulus generator 120 to deliver a stimulus signal to at least one of the flexible electrodes 106A. For example, the controller 130 can be configured to select the parameters of the electrical stimulation (e.g., frequency, current intensity, waveform shape, etc.) similarly as described above. Optionally, the controller 130 can include a display device and/or an input device (e.g., a human machine interface for receiving user commands). Optionally, the controller 130 can include an output device, for example, to provide audible, visible, and/or tactile alarms to the user. Optionally, each of the flexible electrodes 106A can be individually addressable by the controller 130. As described below, the controller 130 can be configured to identify and then supply stimulation signals to a select group of the flexible electrodes 106A (i.e., the set of the flexible electrodes) in order to target vagus nerve activity.

In some implementations, the controller 130 can be further configured to monitor impedance detected at one or more of the flexible electrodes 106A. In some implementations, the controller 130 can be further configured to control pressure of the inflatable cuffs 104A, 104B. For example, the controller 130 can optionally be configured to control pressure of the inflatable cuff 104A based on the detected impedance. Monitoring impedance detected at the flexible electrodes 106A provides an indication as to whether the flexible electrodes 106A have made contact with the subject's tracheal wall. Pressure of the inflatable cuff 104A can be adjusted up or down based on this feedback.

In some implementations, the controller 130 can be further configured to identify the set of the flexible electrodes 106A by sequentially delivering test stimulus signals to one or more of the flexible electrodes 106A and monitoring the subject's physiological feedback signal detected in response thereto. In this way, the controller 130 can determine which subset of flexible electrodes 106A anatomically align with a region of the tracheal wall for selectively targeting vagus nerve activity. This disclosure contemplates that delivering stimulation to specific flexible electrodes that anatomically align with the region of the tracheal wall for selectively targeting vagus nerve activity will cause a change in physiological feedback signal. On the other hand, delivering stimulation to flexible electrodes that do not anatomically align with this specific region will not cause such a change in physiological feedback signal. The physiological feedback signal can be an electrocardiogram, encephalogram, arterial pressure, or galvanic skin response. It should be understood that an electrocardiogram, encephalogram, arterial pressure, or galvanic skin response are only provided as example physiological feedback signals and that this disclosure contemplates monitoring other physiological feedback signals.

In some implementations, the controller 130 can be further configured to control the stimulus generator 120 to deliver a stimulus signal to the set of the flexible electrodes 106A, and the stimulus signal can be configured to stimulate the vagus nerve and/or surrounding tissue structures. Optionally, the controller 130 can be further configured to optimize at least one parameter of the stimulus signal by monitoring the subject's physiological feedback signal. For example, the controller 130 can optimize a frequency or current intensity of the stimulus signal. It should be understood that frequency and current intensity of the stimulus signal are only provided as example parameters and that this disclosure contemplates optimizing other parameters of the stimulus signal. Alternatively or additionally, the controller 130 can optimize a number of electrodes in the set of the flexible electrodes 106A, which are used to deliver the stimulus signal. As described herein, the stimulus signal can target the subject's vagus nerve and/or any surrounding tissue structures. In some implementations, a first stimulus signal can be used to target the subject's vagus nerve, and a second stimulus signal can be used to target the surrounding tissue structures. In other words, a plurality of stimulus signals can be used in combination in some implementations. The controller 130 can therefore be configured to optimize the stimulus signal for individual patients. Alternatively or additionally, the controller 130 can also be configured to select parameters for the stimulus signal based on which medical condition is being treated. It should be understood that parameters of the stimulus signal can vary based on the patient (and even over time for the same patient) and/or based on the medical condition.

Figure 1B:
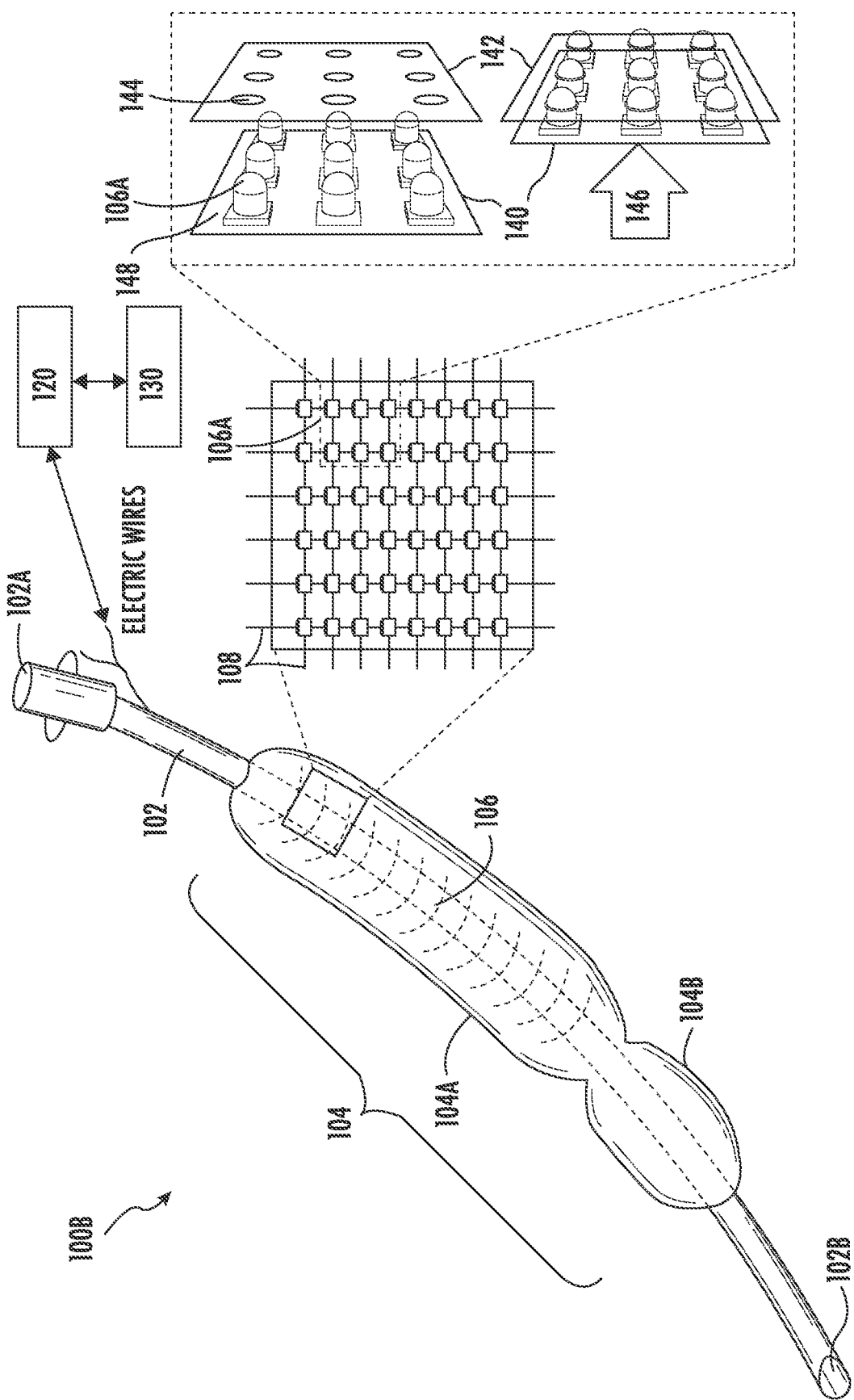
FIG. 1B is a diagram of another example endotracheal device according to an implementation described herein.

Referring now to FIG. 1B, another example endotracheal device 100B (e.g., an nSIM device) is shown. The endotracheal device 100B can include an elongate tubular member 102 having a proximal end 102A and a distal end 102B. The endotracheal device 100A can also include an inflatable cuff 104 arranged between the proximal and distal ends of the elongate tubular member 102, and an electrode array 106 disposed in proximity to an exterior surface of the inflatable cuff 104. The inflatable cuff 104 can be configured to expand to contact a subject's tracheal wall. In some implementations, the endotracheal device 100B can include inflatable cuff 104A and holding cuff 104B. The endotracheal device 100B can further include a stimulus generator 120 operably coupled with the electrode array 106, e.g., using a plurality of flexible conductors 108. Additionally, the endotracheal device 100B can further include a controller 130 operably coupled with the stimulus generator 120. It should be understood that the above features of the endotracheal device 100B are also described above with regard to FIG. 1A.

In FIG. 1B, the inflatable cuff 104 includes a first inflatable portion 140 (e.g., inner) and a second inflatable portion 142 (e.g., outer). The second inflatable portion 142 is arranged around the first inflatable portion 140. Each of the first and second inflatable portions 140, 142 can optionally be configured for independent pressure regulation. For example, each of the first and second inflatable portions 140, 142 can have separate tubing and/or pressure regulators for inflation. As shown in FIG. 1B, the first inflatable portion 140 includes the electrode array 106 with the plurality of flexible electrodes 106A, and the second inflatable portion 142 includes a plurality of openings 144 corresponding to the flexible electrodes 106A. This disclosure contemplates that the openings 144 are sized such that it is possible to inflate the second inflatable portion 142. Accordingly, the second inflatable portion 142 can be configured to contact the subject's tracheal wall. For example, in some implementations, the second inflatable portion 142 can be a low pressure cuff, which is configured to interact with the mucosa of the subject's tracheal wall. The second inflatable portion 142 can be inflated by the user (e.g., medical professional) during intubation. Prior to delivery of stimulation, the first inflatable portion 140 can also be inflated by the user (e.g., medical professional). As the first inflatable portion 140 is inflated, the flexible electrodes 106A extend through the corresponding openings 144 of the second inflatable portion 142 to contact the subject's tracheal wall. Arrow 146 in FIG. 13 illustrates inflation of the first inflatable portion 140 such that the flexible electrodes 106A extend through the corresponding openings 144 of the second inflatable portion 142.

In some implementations, the first inflatable portion 140 can include a plurality of protrusions 148, and the flexible electrodes 106A can be patterned on a surface of the protrusions 148. For example, the protrusions 148 can be relatively soft, flexible knobs provided on a substrate. The protrusions 148 can be sized and/or shaped to maintain contact with the patient's tracheal wall. In some implementations, the protrusions 148 can have a rounded shape as shown in FIG. 1B. Optionally, the protrusions 148 can be formed (e.g., by molding, additive manufacturing, subtractive manufacturing, etc.) from a polymer. The flexible electrodes 106A can then be patterned (e.g., deposited, plated, printed, etc.) onto the protrusions 148. As described above, the flexible electrodes 106A can optionally be formed from EMC and/or radio translucent materials. It should be understood that the size, shape, and/or materials used for the protrusions 148 and flexible electrodes 106A are provided only as examples.

Figure 2:
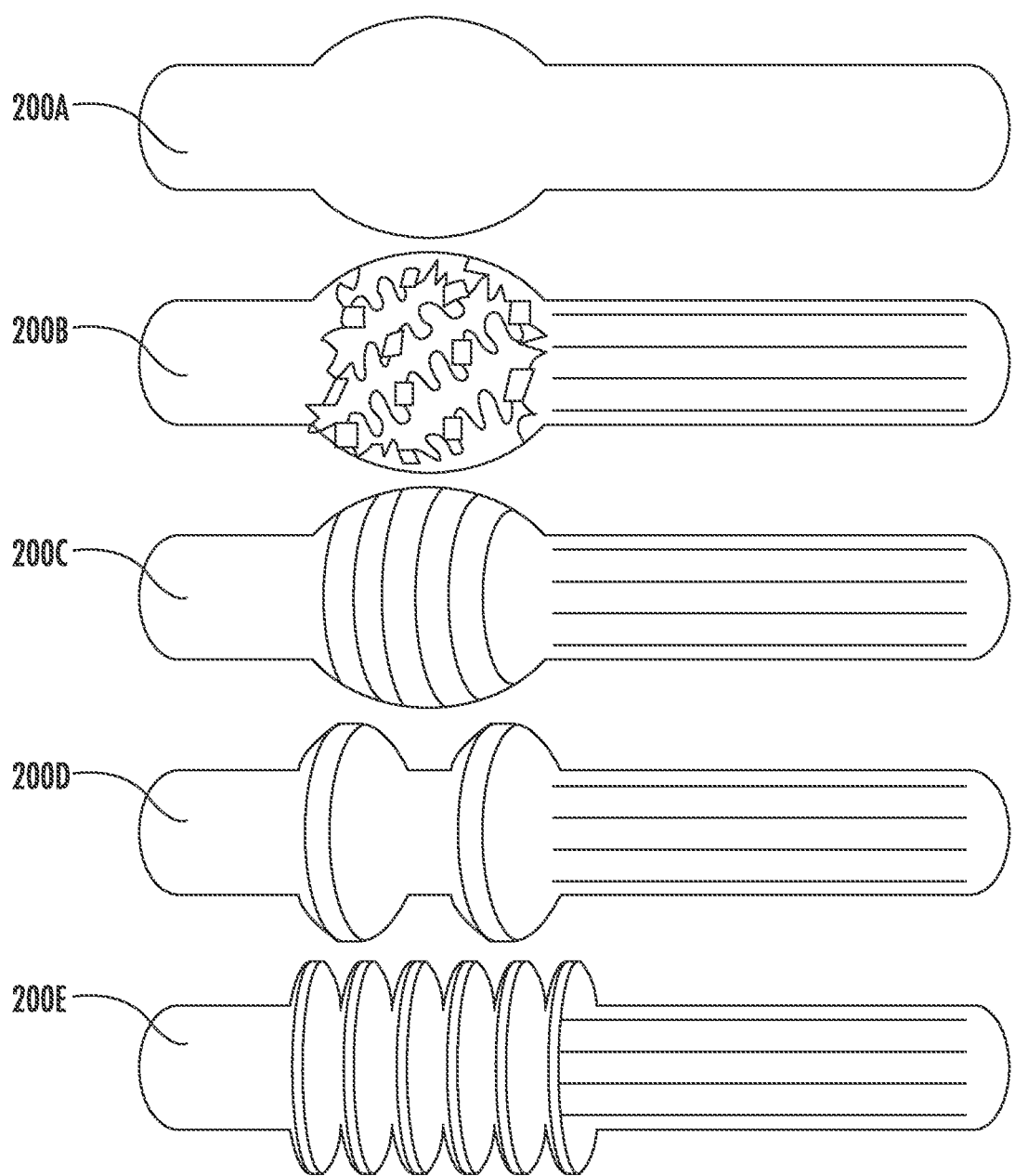
FIG. 2 illustrates example endotracheal devices according to implementations described herein.

Referring now to FIG. 2, example endotracheal devices 200A-200E according to other implementations are shown. The endotracheal devices 200A-200E can include electrode array designs with flexible electrodes and wires (e.g., flexible conductors) in concentric circles or a spiral pattern to allow expansion and significant trachea coverage. Electrode placement can be focused on the cuff surface where the contact with vagus nerve at the intersection of the trachea is most likely. In some implementations, designs include the use of multiple expansion cuffs. Discrete cuffs with electrode array coverage can allow the select inflation at the zone of best nerve interface and also provide the ability to control the pressure against the trachea surface without affecting the function seal of the endotracheal tube. Endotracheal device 200B includes an electrode array with expanding stent coils. Endotracheal device 200C includes an electrode array with flexible spiral wires with parced microelectrodes. Endotracheal device 200D includes an electrode array with flexible spiral wires and a plurality (e.g., two) independent inflatable cuffs. Endotracheal device 200E includes an electrode array with flexible spiral wires and a plurality (e.g., six) independent inflatable cuffs. It should be understood that the number of inflatable cuffs should not be limited by the examples shown in FIG. 2.

Example Computing Device

It should be appreciated that the logical operations described herein with respect to the various figures may be implemented (1) as a sequence of computer implemented acts or program modules (i.e., software) running on a computing device (e.g., the computing device described in FIG. 3), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Figure 3:
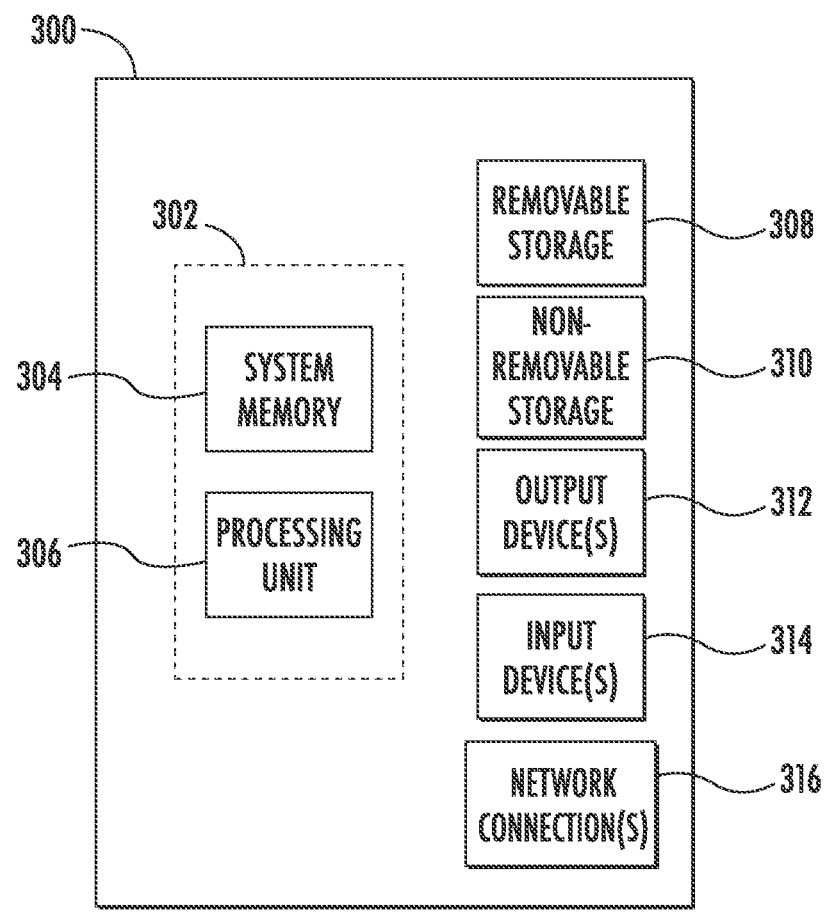
FIG. 3 is a block diagram of an example computing device.

Referring to FIG. 3, an example computing device 300 upon which embodiments of the invention may be implemented is illustrated. It should be understood that the example computing device 300 is only one example of a suitable computing environment upon which embodiments of the invention may be implemented. Optionally, the computing device 300 can be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In its most basic configuration, computing device 300 typically includes at least one processing unit 306 and system memory 304. Depending on the exact configuration and type of computing device, system memory 304 may be volatile (such as random access memory (RAM)), non-volatile (such as read-only memory (ROM), flash memory, etc.), or some combination of the two. This most basic configuration is illustrated in FIG. 3 by dashed line 302. The processing unit 306 may be a standard programmable processor that performs arithmetic and logic operations necessary for operation of the computing device 300. The computing device 300 may also include a bus or other communication mechanism for communicating information among various components of the computing device 300.

Computing device 300 may have additional features/ functionality. For example, computing device 300 may include additional storage such as removable storage 308 and non-removable storage 310 including, but not limited to, magnetic or optical disks or tapes. Computing device 300 may also contain network connection(s) 316 that allow the device to communicate with other devices. Computing device 300 may also have input device(s) 314 such as a keyboard, mouse, touch screen, etc. Output device(s) 312 such as a display, speakers, printer, etc. may also be included. The additional devices may be connected to the bus in order to facilitate communication of data among the components of the computing device 300. All these devices are well known in the art and need not be discussed at length here.

The processing unit 306 may be configured to execute program code encoded in tangible, computer-readable media. Tangible, computer-readable media refers to any media that is capable of providing data that causes the computing device 300 (i.e., a machine) to operate in a particular fashion. Various computer-readable media may be utilized to provide instructions to the processing unit 306 for execution. Example tangible, computer-readable media may include, but is not limited to, volatile media, non-volatile media, removable media and non-removable media implemented in any method or technology for storage of information such as computer readable instructions, data structures, program modules or other data. System memory 304, removable storage 308, and non-removable storage 310 are all examples of tangible, computer storage media. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 306 may execute program code stored in the system memory 304. For example, the bus may carry data to the system memory 304, from which the processing unit 306 receives and executes instructions. The data received by the system memory 304 may optionally be stored on the removable storage 308 or the non-removable storage 310 before or after execution by the processing unit 306.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

Example Methods

Figure 4:
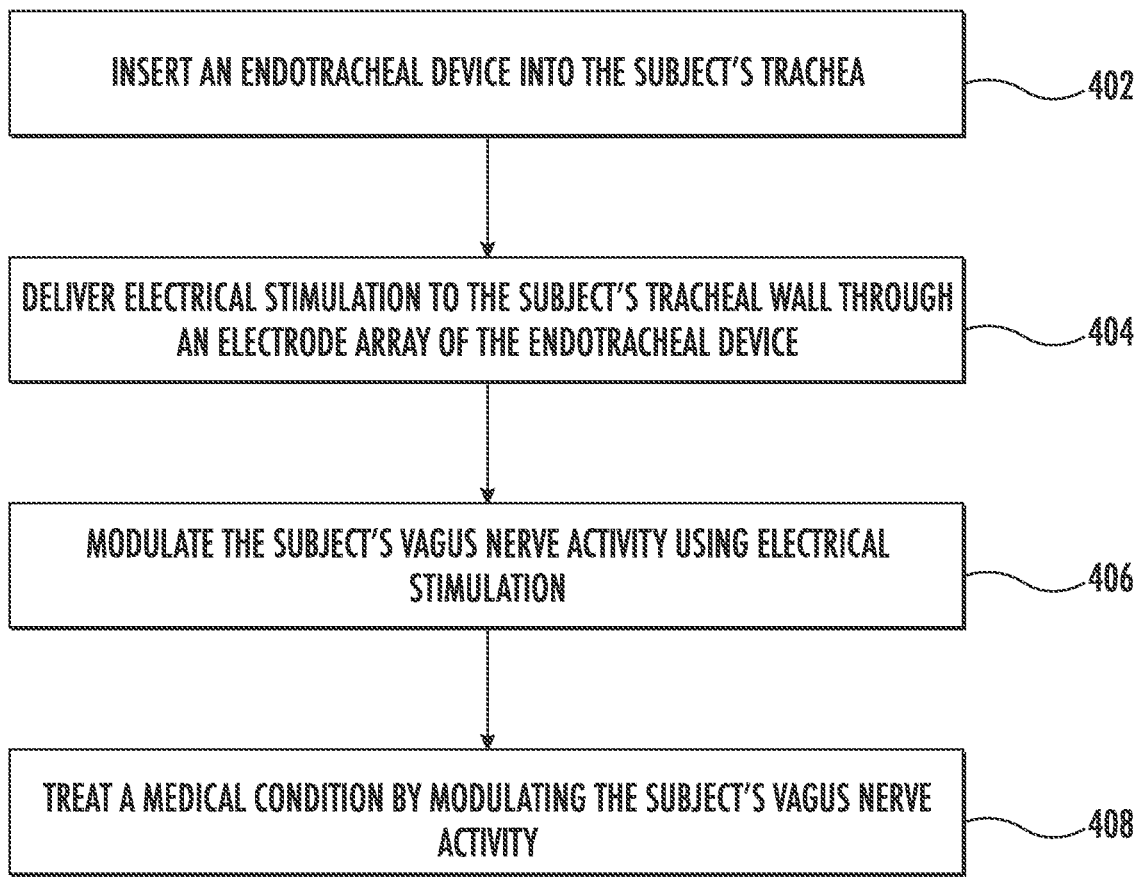
FIG. 4 is a flow diagram illustrating example operations for using an endotracheal device according to an implementation described herein.
Figure 5:
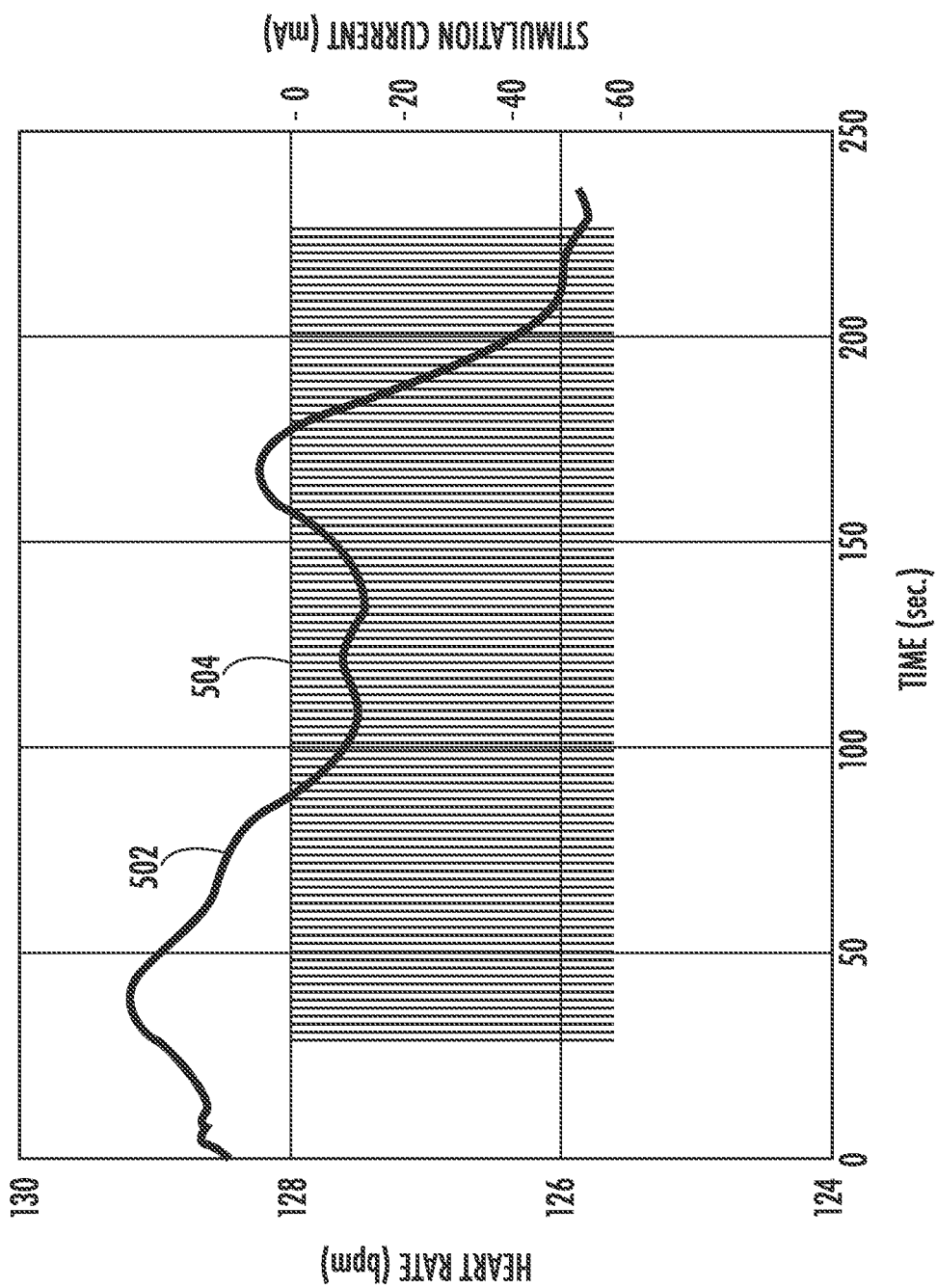
FIG. 5 is a graph illustrating the effect of trans-tracheal vagus nerve stimulation using an nSIM device (e.g., the endotracheal device shown in FIGS. 1A-1B) on heart rate.
Figure 6:
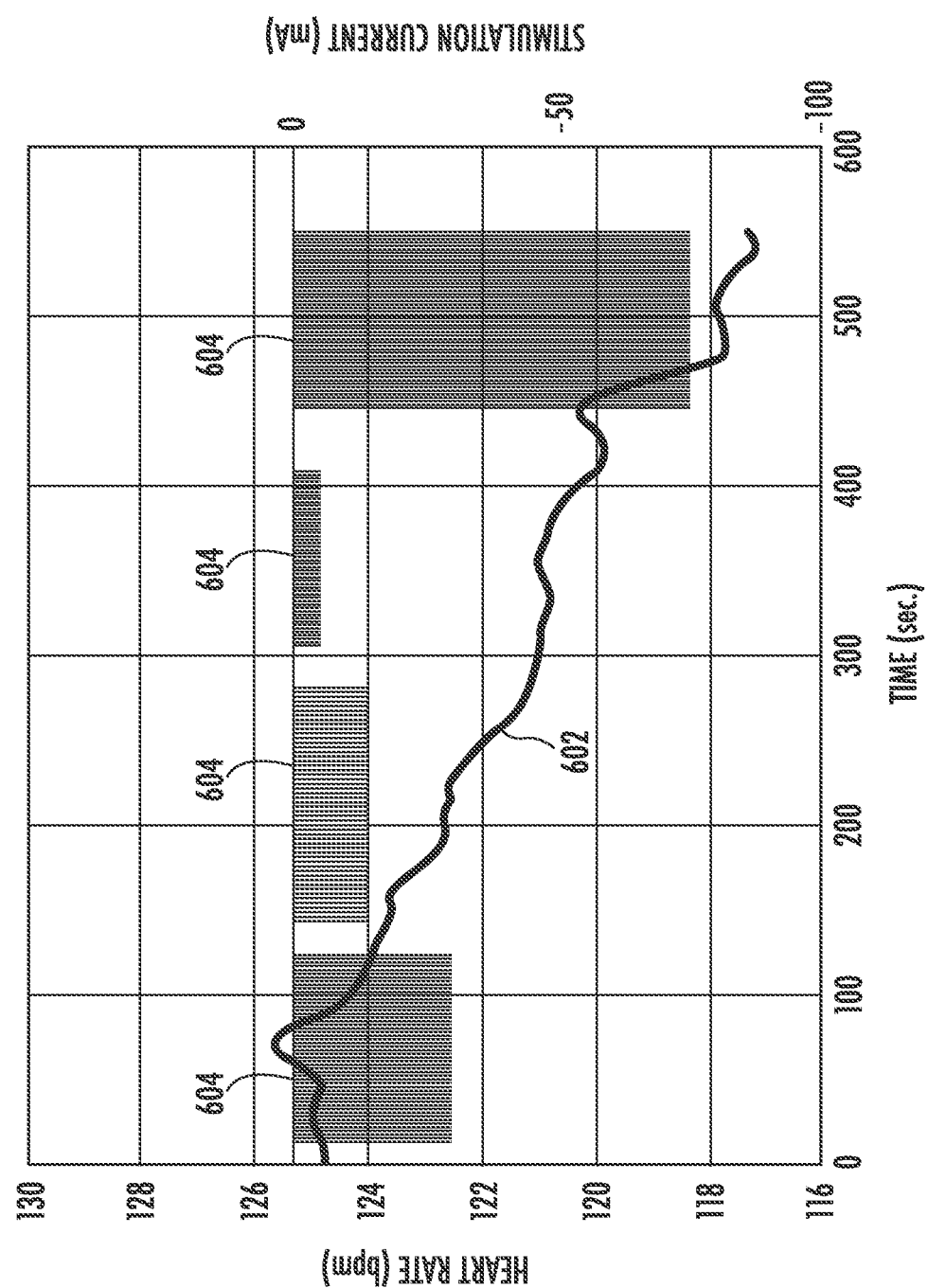
FIG. 6 is a graph illustrating the effect of trans-tracheal vagus nerve stimulation using nSIM device (e.g., the endotracheal device shown in FIGS. 1A-1B) on heart rate at different current intensities.
Figure 7:
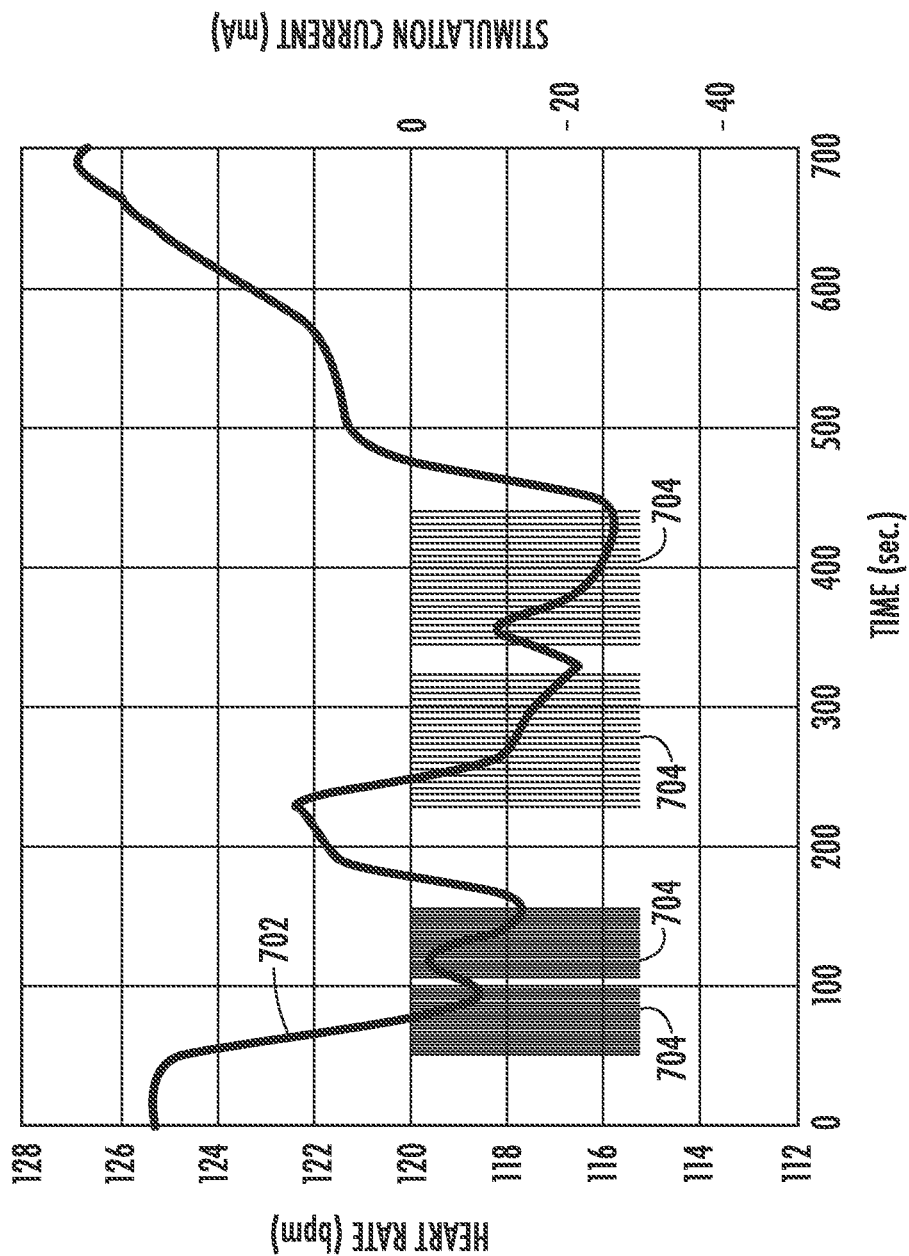
FIG. 7 is a graph illustrating the effect of direct vagus nerve stimulation using conventional nerve cuff electrodes on heart rate.

Referring now to FIG. 4, example operations for modulating vagus nerve activity are shown. At 402, an endotracheal device (e.g., endotracheal device 100A or 100B of FIGS. 1A-1B) can be inserted into the subject's trachea. At 404, electrical stimulation can be delivered to the subject's tracheal wall through an electrode array (e.g., electrode array 106 of FIGS. 1A-1B) of the endotracheal device. At 406, the subject's vagus nerve activity can be modulated using the electrical stimulation. As described above, the electrical stimulation can target the vagus nerve and/or surrounding tissue structures. The endotracheal device described herein can access the subject's vagus nerve network almost non-invasively (e.g., intubation only). And, because intubation is part of the standard of care (SOC) for many medical conditions (e.g., stroke), the endotracheal device does not interfere with SOC. Optionally, at 408, a medical condition can be treated by modulating the subject's vagus nerve activity. For example, the medical condition can be stroke, traumatic brain injury, shock, hemorrhage, general surgery, brain and spinal surgery, a general anesthesia procedure, cardiac surgery, cardiac surgery under cardiopulmonary bypass, extracorporeal bypass surgery, or comatose state.

This disclosure contemplates that procedures (e.g., medical procedures and/or surgeries described above) can be elective or emergent. In some implementations, the medical condition is a transient condition and presents during a post surgical recovery period. This disclosure contemplates that the post surgical recovery period can last any amount of time (e.g., hours, days, weeks, etc.). In other implementations, the medical condition is a long term condition such as a comatose or vegetative state, for example. Electrical stimulation can be delivered one time or repeatedly (e.g., recurrent stimulation) to treat the medical condition.

In some implementations, the method can further include tailoring at least one parameter of the electrical stimulation based on the medical condition or surrounding tissue structures to be modulated. It should be understood that parameters of the electrical stimulation can vary based on the medical condition. The parameter can include, but is not limited to, a frequency, a current intensity, or a number of electrodes in the set of the flexible electrodes.

In some implementations, the method can further include monitoring a physiological feedback signal of the subject.

For example, the physiological feedback signal can be an electrocardiogram, encephalogram, arterial pressure, or galvanic skin response. It should be understood that an electrocardiogram, encephalogram, arterial pressure, or galvanic skin response are only provided as example physiological feedback signals and that this disclosure contemplates monitoring other physiological feedback signals. Alternatively or additionally, the method can further include tailoring at least one parameter of the electrical stimulation based on the physiological feedback signal. It should be understood that parameters of the electrical stimulation can vary based on the patient (and even over time for the same patient).

Examples

Published data indicates that direct manipulation of vagal electrical activity has remarkable therapeutic potential for the modulation of inflammation, control of brain perfusion pressure, reduction of edema, and facilitation of endogenous repair in the setting of brain injury and stroke. As described herein, there is potential for stimulating the vagal nerve in the acute period following stroke or during any surgical procedure that puts the brain at risk of secondary injury. Evidence collected during studies, as well as published data, indicate maximal benefit occurs in the acute period or phase. A major barrier to the application of nerve stimulation therapy during the acute phase is the need for effective therapy to be applied intimately at the nerve surface, which to date requires a surgical procedure that would put patients at further risk. Additionally, such surgical procedure cannot be applied within the surgical arena where it could do the most benefit due to time and technical constraints.

The nSIM devices described herein eliminate these barriers. In particular, the nSIM devices described herein can be used to semi-noninvasively (e.g., intubation only) stimulate the patient's vagus nerve and/or surrounding tissue structures within the intensive care or surgical arena where it will have the most impact. While numerous conventional devices have been proposed for the modulation of the vagus nerve activity, to date, no device has been developed that effectively can modulate vagal nerve activity by fitting seamlessly into the standard of care (SOC) for stroke, injury, and surgical cases. Specifically, a new approach to the modulation of the vagus nerve activity for the conditions which, first, benefit from modulation of vagus nerve activity and, second, require intubation as part of the standard of care is proposed. Endotracheal intubation is employed in many groups of patients including, but not limited to, surgery, various emergency conditions such as traumatic brain injury, stroke, hemorrhagic shock, "crush" syndrome, etc. In most of these conditions, endotracheal modulation/stimulation of vagus nerve activity can have therapeutic effect, as well as adjuvant therapeutic properties to improve the patient's conditions, to prevent complications development, to accelerate recovery, etc. Currently, pharmacological therapies are applied in the acute setting to control blood pressure, cerebral perfusion pressure, and inflammation and other vital functions, but these parameters change rapidly and have significant overshoot with pharmacotherapy. Much of the needs of cerebral perfusion and inflammation can be more dynamically and directly controlled through nerve stimulation.

An nSIM device is described herein, e.g., an endotracheal tube, such as endotracheal tube 100A or 100B of FIGS. 1A-1B, equipped with a plurality of flexible electrodes (e.g., an electrode array) that stretch and provide complete coverage of the area of the trachea where vagal nerve activity can be sensed and modified. The electrode array is a stretchable, thin electrode array that does not interfere with the normal function or placement of the endotracheal tube. Additionally, the electrode array can accommodate the variable anatomy that patients present, as well as the relatively small but intimate target that the vagal nerve interacts at the trachea wall. Additionally, the thin, stretchable electrodes can be adapted for modulation of the activity of other than vagus nerves, such as sympathetic ganglia, which opens the potential for the development of new nerve modulating therapeutic modalities.

Some conventional technologies for delivering stimulation in a patient's trachea are designed for sensing vocal cords for protection of the functions of the esophagus and trachea during surgery. These vocal cord stimulation technologies, however, do not incorporate a method to selectively stimulate across the entire surface of the endotracheal tube, precluding their use for select stimulation. Locating, recording and stimulating the vagal target is facilitated by a method to assess the function of the nerve simultaneously. A number of variations in endotracheal tube design have been proposed (e.g., endotracheal devices of FIGS. 1A, 1B, and 2). These variations have been used to test and configure for optimal use in human subjects. Due to the placement of the flexible electrode array, it is possible to activate discrete electrodes for stimulation for effect of respiratory pathways as well as vagal and sympathetic nerves innervating esophagus, which will have additional therapeutic effects.

The nSIM devices described herein can leverage real-time feedback control of electrical stimulation of the vagus nerve. In particular, the nSIM devices can be tethered to existing patient data to actively generate stimulating currents and deliver them to the endotracheal tube electrodes with adjustment by biological parameters, such as electroencephalogram, galvanic skin response, electrocardiogram, etc. In addition to accurate location and sensing of the vagal nerve, therapeutic stimulation can be modified based on the modality (e.g., stroke, traumatic brain injury (TBI), shock, hemorrhage, surgery, comatose state, etc.) and individual patient sensitivity to the stimulation. The stimulation regiment generated by the nSIM devices can use algorithms to optimize the stimulation in each patient and for each medical condition or disease.

The nSIM device can be an electrical modulator of nerve activity through a compliant spiral or loop arrays of electrodes (e.g., flexible electrodes 106A of FIGS. 1A-1B) localized on the endotracheal tube (e.g., endotracheal devices of FIGS. 1 and 2). Electrical current applied to the inner surface of laryngopharynx, trachea, bronchi, or esophagus can modulate activity of the nerves innervating these subdivisions of the respiratory pathways as well as anatomically adjacent nerve ganglia, such as sympathetic ganglia. The surface of the trachea where vagal nerve stimulation should be most effective is at the position of the inflatable cuff based on human anatomy. In addition, the combination of endotracheal tube located electrodes and surface electrodes can optionally provide stimulation of sympathetic ganglia and additional nerves.

nSIM devices can include, but are not limited to, the endotracheal tube equipped with an array of electrodes located on the single or multiple inflatable cuffs (e.g., endotracheal devices 200A-200E of FIG. 2) in such a way that when cuffs are inflated the stable electrical contact between the inner surface of the respiratory pathways and the cuff surface electrodes is formed. Inflatable cuffs with the surface electrodes can be single or multiple, concentric or spiral, and the surface electrodes can be distributed along the length of the endotracheal tube. One advantageous aspect of the design is the concentric distribution of surface electrodes that expand with the cuff thus creating a near uniform distribution of sensing and stimulating electrode recovery. This design facilitates the function of the nSIM device to accommodate or adapt to varying anatomy of the human neck and chest and the possible shifting or need to shift or reposition the endotracheal tube during patient therapy. A spiral or concentric array on a single or multiple expanding cuffs allows the user to adapt or target sensing and stimulation to the precise location needed. This effect cannot be routinely applied with large or widely spaced electrodes that do not conform or stretch. Optionally, the electrode material can be magnetically compatible to allow MRI of the patient. Optionally, the electrode material can be radio translucent to not interfere with the need for intraoperative imaging.

The nSIM device can include a control unit (e.g., stimulus generator 120 and/or controller 130 of FIGS. 1A-1B) that generates electric current delivered to the electrodes. The control unit is capable of generating various forms of electrical currents distributed between individual electrodes, or combinations of electrodes, on the surface of the cuff(s) of the endotracheal tube. The specific characteristics of the stimulating currents depends on the therapeutic indication and feedback from the various sources such as electroencephalographic, electrocardiographic, signals, changing in galvanic skin response, and/or mechanical pulsations (e.g., physiological feedback signals). Base stimulation have been developed and tested in research in animals and will be used for initial nerve activation with subsequent modification based on anatomy and physiology of the individual patient. The control unit contains a microprocessor with stimulation diagnostic sequences to determine the electrode contact resistance and preprogrammed stimulation regiments, including an automated sequence to determine the optimal stimulation for the specific indication. Regiments of stimulation can be adjusted based on the feedback signals (e.g., physiological signals from patient) to optimize efficacy of the delivered stimulation depending on the therapeutic purpose and individual anatomy/sensitivity. The control unit also allows manual control of stimulation. The control unit is equipped with a display to provide information on the ongoing stimulation parameters, as well as status of feedback signals. Conventional vagal stimulators lack feedback control, which significantly decreases their potential to effectively function in the acute trauma or stroke patient where vital functions should be continuously monitored and modified.

It has been established that stimulation of specific brain sites such as cerebellar fastigial nucleus, sub thalamic vasodilator area, rostral ventrolateral medulla as well as pterygopalatine ganglion and trigeminal nerve innervated skin areas are capable to exert powerful neuroprotective effect against stroke and traumatic brain jury. For example, clinical management of stroke can be transformed by introducing the nSIM devices described herein as adjuvant therapy at the moment of intubation during acute care of National Institutes of Health Stroke Scale (NIHSS)>6 candidates for thrombectomy. Based on data and available literature, tracheal stimulation using an endotracheal tube can likely afford neuroprotective (stroke, traumatic brain injury, subarachnoid hemorrhage, etc.), anti-inflammatory, antiepileptic and other beneficial therapeutic effects. The nSIM devices described herein can therefore be used in various conditions, from emergency care to prolonged therapy of comatose patients. The nSIM devices described herein cross the many clinical barriers that prevent nerve stimulation in the acute setting of stroke and post-stroke surgical therapy such as thrombectomy.

A major technical barrier to therapeutic stimulation of brain function in the acute setting of trauma, stroke, and complications from surgery is the complexity of the medical system that prevents secondary acute surgeries and also presents a variety of physical and electronic barriers to invasive devices. The nSIM devices described herein solve these problems by seamlessly fitting in to the standard of care (SOC). The nSIM devices described herein can be preinstalled on an endotracheal tube and thereby entered into the medical care pipeline of various diseases or trauma improving current treatment standards. This is a n approach that allows an aggressive and intensive sensing and management of nerve activity that can be delivered in a flexible device that can reach the nerve fibers that are difficult to target and exhibit anatomical variability. A thin, flexible electrode with a spiral, annular, or concentric, expanding electrode coverage surface that stretches with the inflated cuff or cuffs can facilitate delivery of the therapy in the intensive care unit, in the surgical arena, and post-surgical care without a second surgery or bulky device that would not fit within the existing technologies. Direct activation and modulation of neural function, blood pressure, brain perfusion pressure, and neuroprotection signals can significantly reduce or eliminate the formerly irreversible or uncontrollable neuronal damage that occurs inadvertently in surgery, cerebrovascular diseases, trauma and other central nervous system (CNS) impairments.

An example method of using the nSIM devices described herein, such as the endotracheal device of FIGS. 1A and/or 1B, is provided below:

Step 1: Inflation. After the intubation and inflation of the "holding" cuff (e.g., holding cuff 104B of FIGS. 1A-1B) of the endotracheal device (e.g., endotracheal device 100A of FIGS. 1A-1B), the main cuff (e.g., inflatable cuff 104A of FIGS. 1A-1B) is inflated by the automated pump while the average impedance at the points of contact of cuff surface electrodes (e.g., flexible electrodes 106A of FIGS. 1A-1B) and the trachea wall reaches levels of single ohms. In parallel resistance between neighbor electrodes is being monitored. As soon as electrode-wall impedance reaches single ohms levels and it is below the resistance between two neighbor electrode inflation stops.

Step 2: Stimulation optimization. After reaching optimal contact between cuff wall electrodes and tracheal mucosa, the controller (e.g., controller 130 of FIGS. 1A-1B) sequentially negotiates electrodes (e.g., flexible electrodes 106A of FIGS. 1A-1B) providing test stimulation and analyzing the feedback signals. Feedback signals include, but not limited by, electrocardiogram, encephalogram, arterial pressure, and/or galvanic skin response. Testing stimulation is initiated at the top of posteriorly located electrodes at the area covering 1 $cm^2$ and current of 50 μA at 10-20 Hz, 500 μS duration of each stimulus delivered in trains of 1 second (sec) with the intertrain interval of 1 second.

Feedback is being monitored for increase of RR interval (i.e., interval between successive Rs or peak of QRS complex of ECG wave) of electrocardiogram (ECG), delta-theta rhythm of encephalogram, and/or increase in galvanic skin response. Stimulation continues by shifting the stimulated area (i.e., changing set of stimulated electrodes) until feedback parameters indicate at least 5% change.

The negotiating of different sets of electrodes continues until the maximum changes of monitored parameters are reached. If necessary, area of stimulation can be increased.

Similarly, parameters of stimulation can be increased (increase of stimulation current for up to 50 mA). Once stimulation parameters, producing changes in monitored signals, are identified, the frequency of stimulation, current intensity, and/or number of stimulating electrodes are optimized to maximize changes in feedback parameters. These processes are done by the controller software in automatic regiment. Different regiments can be selected by the physician depending on the specific pathology: stroke, subarachnoid hemorrhage, traumatic brain injury, open heart surgery, etc.

Step 3: Therapeutic stimulation. As soon as optimal localization and stimulation parameters are identified, continuous stimulation with the optimal parameters is committed. Electrode-mucosa and interelectrode resistance are being continuously monitored to maintain contact of electrodes and the tracheal wall and to avoid accumulation of mucose. If electrode contact is changing the inflation of the cuff can be automatically adjusted by the controller. Increased mucose secretion will be controlled by decreasing stimulation frequency.

In course of therapeutic stimulation, the feedback parameters are continuously monitored and maintained at the pre-set levels, e.g. RR interval below 17 msec, theta-delta power of encephalogram ≥30%. If efficacy of stimulation decreases, the sequences of optimization is initiated: increase in intensity, increase in area of stimulation, adjustment of frequency, changes of the area and site of stimulation as described above. This allows to maintain stimulation within the limits necessary for the most efficient treatment of the current condition.

Neurostimulation of the left branch of vagus nerve can lower heart rate (HR) by enhancing parasympathetic tone, through nerve fibers innervating the atrioventricular (AV) node (Matheny & Shaar, 1997). Referring now to FIGS. 5-9, trans-tracheal stimulation of the left vagus nerve using an nSIM device (e.g., e.g., the endotracheal device shown in FIGS. 1A-1B) has been shown to modulate the heart rate of a Yucatan mini-pig (age=3 years, weight=100 Kgs). Modulation of heart rate via nSIM stimulation is compared to that of direct vagus nerve stimulation using conventional nerve cuff electrodes. In both cases, the heart rate is lowered only temporarily when the stimulation is ON, and turning the stimulation OFF, the normal sinus rhythm is restored. These results validate the safety and feasibility of the nSIM device to non-invasively stimulate the left branch of the vagus nerve.

Figure 8:
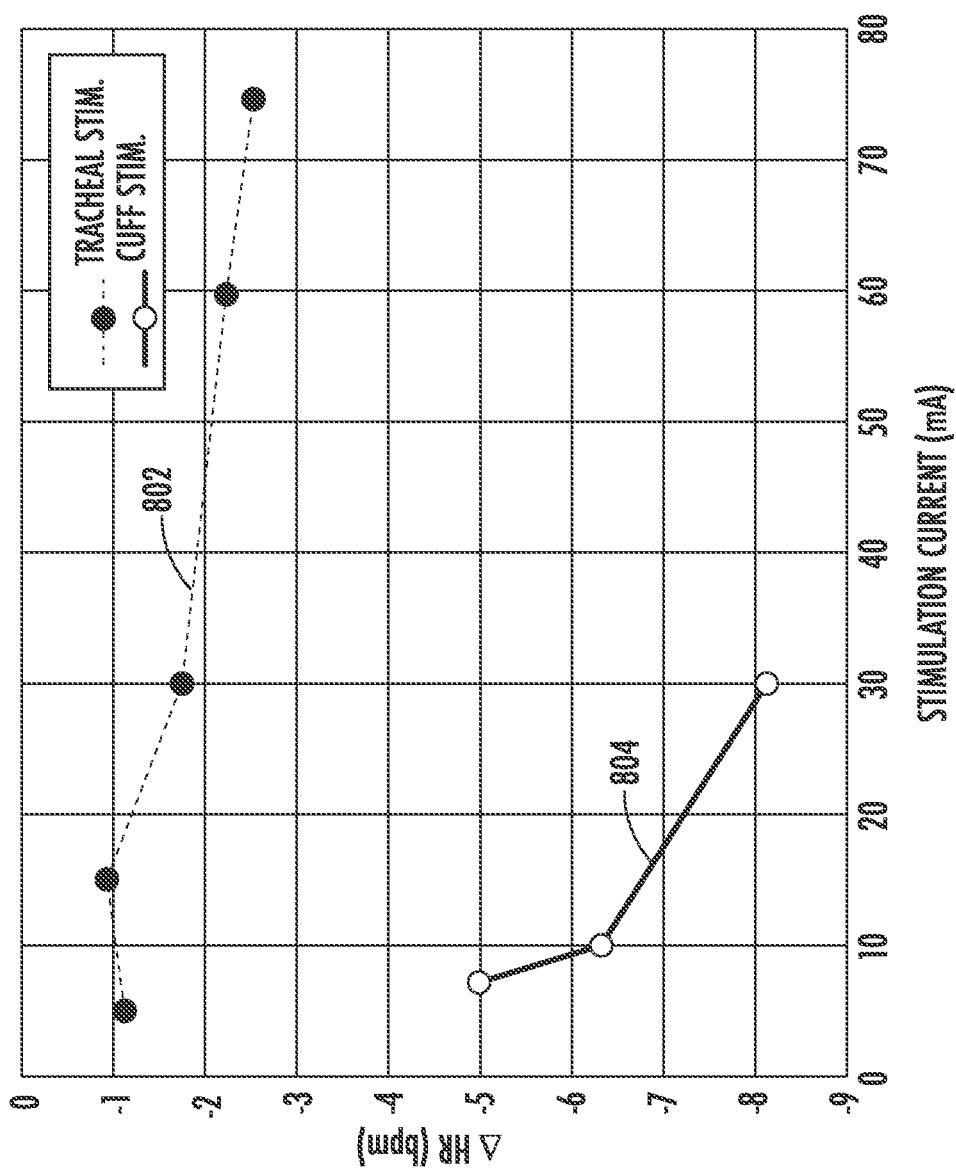
FIG. 8 is a graph illustrating the drop in heart rate as a function of current intensity for tracheal stimulation 802 (e.g., using an nSIM device such as the endotracheal device shown in FIGS. 1A-1B) and conventional nerve cuff stimulation 804 (e.g., using cuff electrodes).
Figure 9:
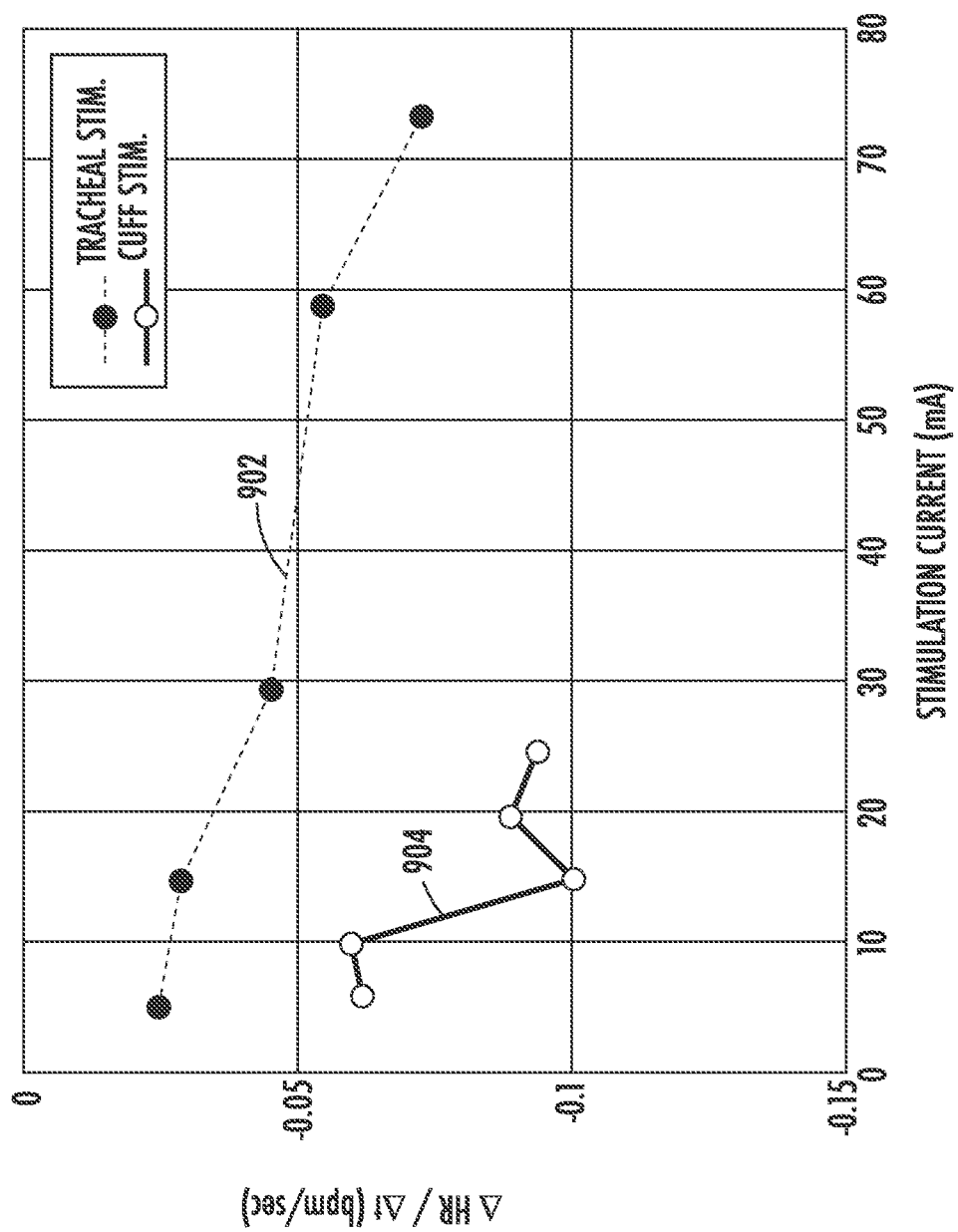
FIG. 9 is a graph illustrating the rate of change of heart rate (e.g. modulation sensitivity) as a function of current intensity for tracheal stimulation 902 (e.g., using an nSIM device such as the endotracheal device shown in FIGS. 1A-1B) and conventional nerve cuff stimulation 904 (e.g., using cuff electrodes). For the measurements shown in FIG. 9, pulse-width was 100 µs and stimulation frequency was 0.5 Hz.

FIGS. 8 and 9 illustrate the drop in heart rate and the rate of change of heart rate, respectively, as a function of current intensity for the different stimulation methods. The equations below were used to quantify heart rate modulation and sensitivity as a function of current intensity:

$$\Delta HR = (\text{Local max.} - \text{Local min.})_T, \text{ where}$$

T is the modulation period in seconds.

$$\Delta T = (T_{Local\ max} - T_{Local\ min})_t, \text{ where}$$

t(i) is the time to reach physiological modulation, and i is the stimulation current.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A system, comprising:
    an endotracheal device comprising:
        an elongate tubular member having a proximal end and a distal end;
        an inflatable cuff arranged between the proximal and distal ends of the elongate tubular member, wherein the inflatable cuff is configured to expand to contact a subject's tracheal wall; and
        an electrode array disposed in proximity to an exterior surface of the inflatable cuff, wherein the electrode array comprises a plurality of flexible electrodes, and wherein a set of the flexible electrodes anatomically align with a region of the subject's tracheal wall for selectively targeting vagus nerve activity;
    a stimulus generator operably coupled with the electrode array; and
    a controller operably coupled with the stimulus generator, the controller comprising a processor and memory operably coupled to the processor, the memory having computer-executable instructions stored thereon that, when executed by the processor, cause the controller to:
        sequentially negotiate the flexible electrodes of the electrode array to identify the set of the flexible electrodes by controlling the stimulus generator to deliver test signals to one or more of the flexible electrodes while monitoring the subject's physiological feedback signal; and
        control the stimulus generator to deliver a stimulus signal to the set of the flexible electrodes, wherein the stimulus signal is configured to modulate vagus nerve activity to achieve a therapeutic purpose.

2. The system of claim 1, wherein each of the flexible electrodes is configured to stretch as the inflatable cuff expands to contact the subject's tracheal wall.

3. The system of claim 1, wherein the flexible electrodes form an annular spiral, concentric, or curved pattern on the exterior surface of the inflatable cuff.

4. The system of claim 1, wherein each of the flexible electrodes has a shape that allows contact with the subject's tracheal wall.

5. The system of claim 4, wherein a diameter or side length of each of the flexible electrodes is between about 0.1 mm and about 1.0 mm.

6. The system of claim 1, wherein the endotracheal device further comprises a plurality of inflatable cuffs arranged between the proximal and distal ends of the elongate tubular member, wherein the electrode array is arranged across respective exterior surfaces of the plurality of inflatable cuffs.

7. The system of claim 1, wherein the inflatable cuff comprises a first inflatable portion comprising the electrode array and a second inflatable portion comprising a plurality of openings corresponding to the flexible electrodes.

8. The system of claim 7, wherein the second inflatable portion is configured to contact the subject's tracheal wall, and wherein the flexible electrodes are configured to extend through the corresponding openings of the second inflatable portion to contact the subject's tracheal wall.

9. The system of claim 7, wherein the first inflatable portion comprises a plurality of protrusions, and wherein the flexible electrodes are patterned on a surface of the protrusions.

10. The system of claim 7, wherein each of the first and second inflatable portions is configured for independent pressure regulation.

11. The system of claim 1, wherein each of the flexible electrodes is individually addressable by the controller.

12. The system of claim 1, wherein the stimulus generator and the electrode array are operably coupled by a plurality of flexible conductors, each respective flexible conductor extending between one or more of the flexible electrodes and the stimulus generator.

13. The system of claim 12, wherein each of the flexible conductors is configured to stretch as the inflatable cuff expands to contact the subject's tracheal wall.

14. The system of claim 1, wherein the memory has further computer-executable instructions stored thereon that, when executed by the processor, cause the controller to monitor impedance detected at one or more of the flexible electrodes.

15. The system of claim 14, wherein the memory has further computer-executable instructions stored thereon that, when executed by the processor, cause the controller to control pressure of the inflatable cuff based on the detected impedance.

16. The system of claim 1, wherein the stimulus signal is configured to stimulate the vagus nerve or surrounding tissue structures.

17. The system of claim 1, wherein the memory has further computer-executable instructions stored thereon that, when executed by the processor, cause the controller to optimize at least one parameter of the stimulus signal by monitoring the subject's physiological feedback signal.

18. The system of claim 17, wherein the at least one parameter comprises a frequency, a current intensity, or a number of electrodes in the set of the flexible electrodes.

19. The system of claim 1, wherein the subject's physiological feedback signal comprises an electrocardiogram, encephalogram, arterial pressure, or galvanic skin response.

20. The system of claim 1, wherein the endotracheal device further comprises a holding inflatable cuff arranged distally with respect to the inflatable cuff, wherein the holding inflatable cuff is configured to secure the elongate tubular member within the subject's trachea.

21. The system of claim 1, wherein the flexible electrodes are formed of an electromagnetically compatible (EMC) material compatible with magnetic resonance imaging (MRI).

22. The system of claim 1, wherein the flexible electrodes are formed of a radio translucent material.

23. The system of claim 1, wherein the therapeutic purpose is at least one of a neuroprotective, neurostimulating, anti-inflammatory, or antiepileptic effect.

24. The system of claim 1, wherein the stimulus signal is configured to modulate vagus nerve activity to achieve the therapeutic purpose without inducing cardiac arrest.

25. The system of claim 1, wherein the memory has further computer-executable instructions stored thereon that, when executed by the processor, cause the controller to, in response to the subject's physiological feedback signal deviating from a pre-set threshold during therapy, repeat the step of sequentially negotiating the flexible electrodes of the electrode array to identify the set of the flexible electrodes.

* * * * *